(12) United States Patent
Berndt et al.

(10) Patent No.: US 7,998,437 B2
(45) Date of Patent: Aug. 16, 2011

(54) MICROFLUIDIC ASSEMBLY WITH COUPLED MICROFLUIDIC DEVICES

(75) Inventors: Manfred Berndt, Karlsbad (DE); Marcus Gassmann, Karlsruhe (DE)

(73) Assignee: Agilent Technologies, Inc., Santa Clara, CA (US)

( * ) Notice: Subject to any disclaimer, the term of this patent is extended or adjusted under 35 U.S.C. 154(b) by 805 days.

(21) Appl. No.: 11/707,429

(22) Filed: Feb. 16, 2007

(65) Prior Publication Data

US 2007/0154355 A1     Jul. 5, 2007

Related U.S. Application Data

(63) Continuation of application No. PCT/EP2004/051834, filed on Aug. 18, 2004.

(51) Int. Cl.
*B01L 3/00* (2006.01)

(52) U.S. Cl. ......... 422/539; 422/503; 422/538; 422/544

(58) Field of Classification Search ........... 422/400, 422/500–544

See application file for complete search history.

(56) References Cited

U.S. PATENT DOCUMENTS

| 6,293,012 | B1 * | 9/2001 | Moles .................. 29/890.124 |
| 6,533,914 | B1 | 3/2003 | Liu |
| 2003/0012697 | A1 | 1/2003 | Hahn et al. |
| 2004/0119070 | A1 | 6/2004 | Roach et al. |
| 2004/0149943 | A1 * | 8/2004 | Field ............................ 251/11 |

FOREIGN PATENT DOCUMENTS

| EP | 1 221 617 | 12/2001 |
| WO | WO 02/070118 | 9/2002 |

* cited by examiner

*Primary Examiner* — In Suk Bullock
*Assistant Examiner* — Timothy G Kingan
(74) *Attorney, Agent, or Firm* — Perman & Green, LLP

(57) ABSTRACT

A microfluidic assembly (1;57) has at least one microfluidic flow path (17,27,29,35,38;82,85,95) and at least one inlet port (11,13,15;81,97,101) coupled to the flow path (17,27,29,35, 38;82,85,95). The microfluidic assembly (1;57) has a first microfluidic device (7;63) that executes a microfluidic process and has a second microfluidic device (9;61). The microfluidic assembly (1;57) has an interface (5;65). The interface (5;65) couples the first microfluidic device (7;63) and the second microfluidic device (9;61).

19 Claims, 5 Drawing Sheets

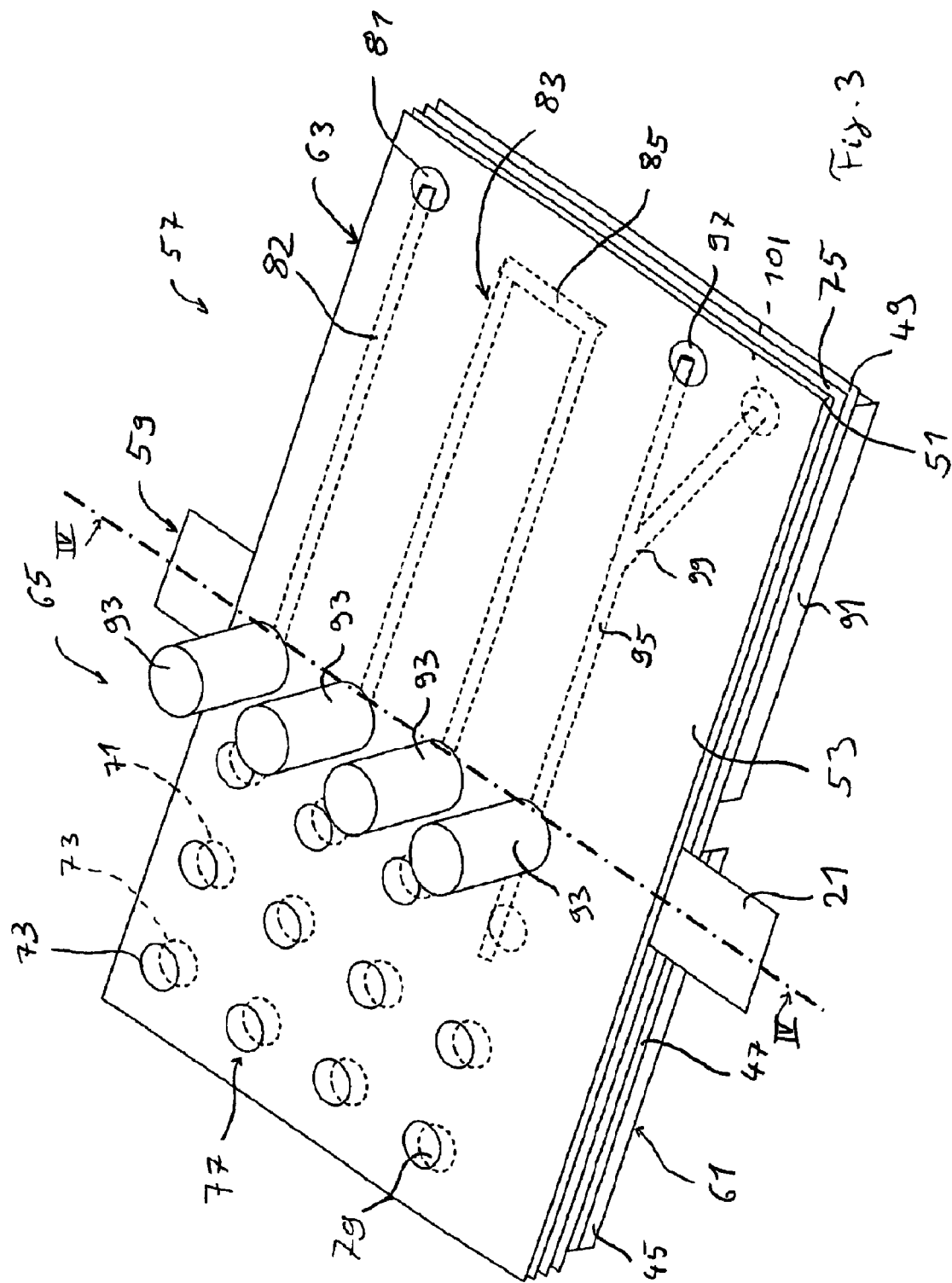

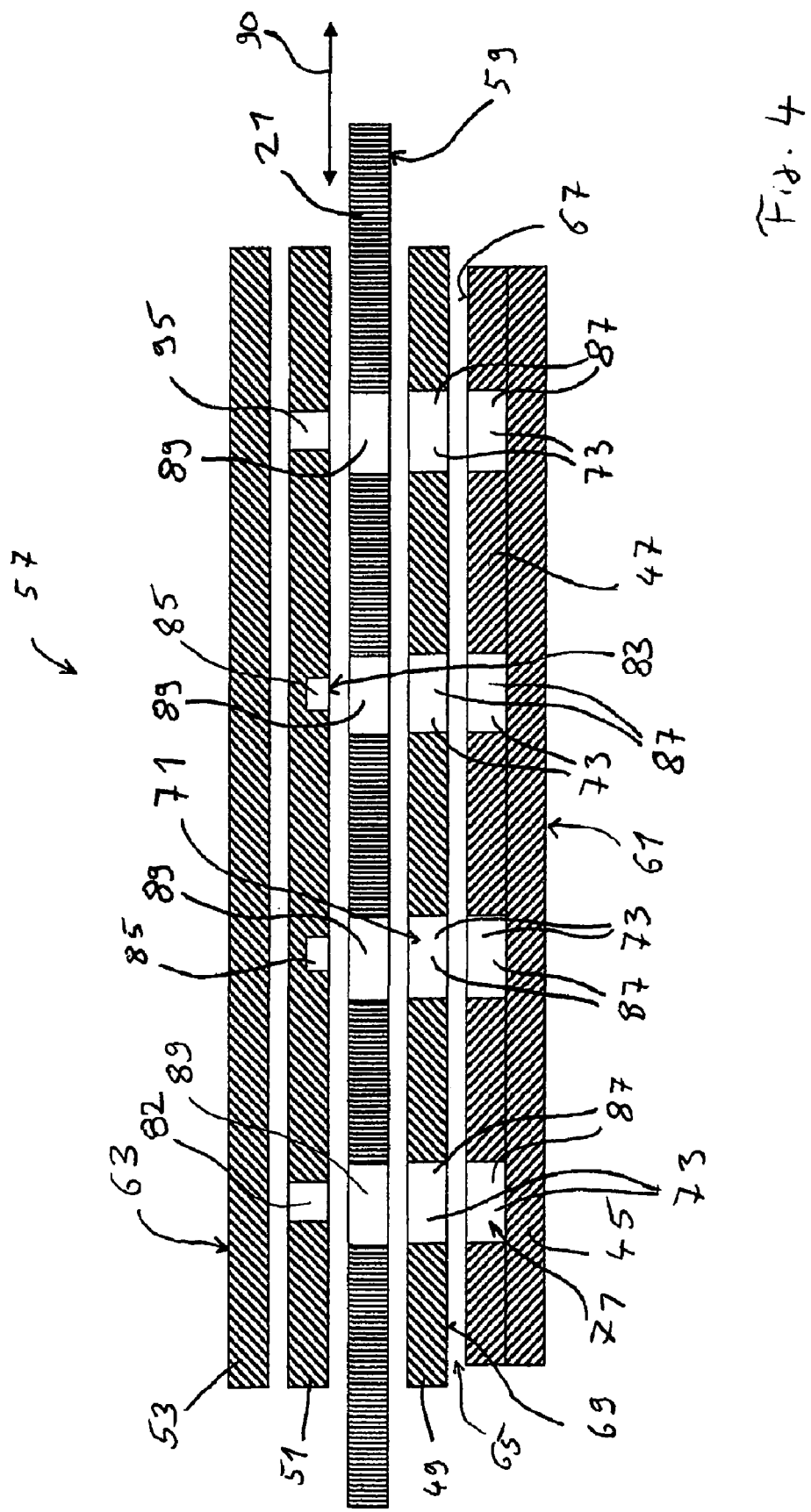

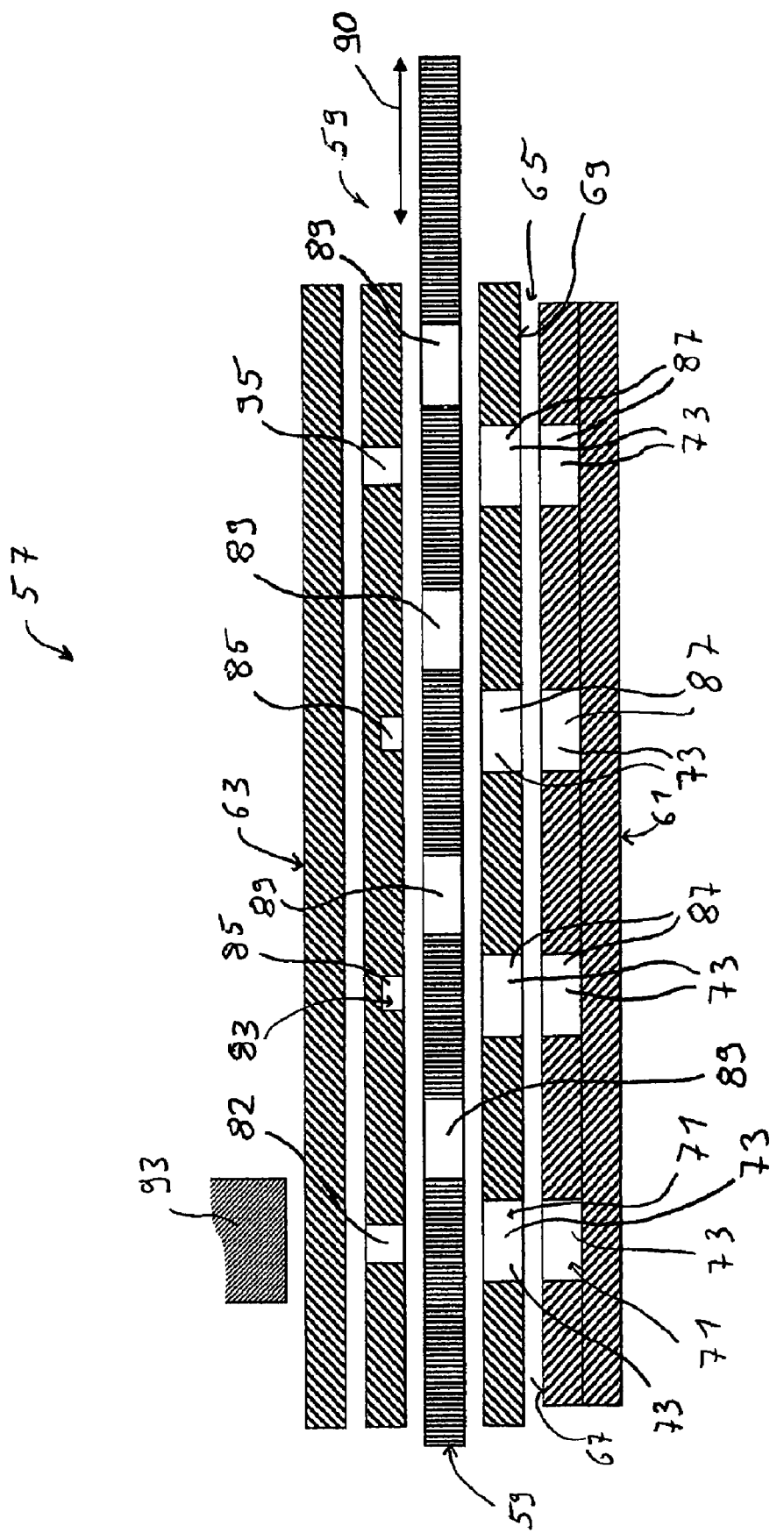

MICROFLUIDIC ASSEMBLY WITH COUPLED MICROFLUIDIC DEVICES

This application is a continuation of International Application No. PCT/EP2004/051834, filed on 18 Aug. 2004, which designated the United States of America, and which international application was published as WO Publication No. WO 2006/018044.

BACKGROUND ART

The present invention relates generally to microfluidic devices and to methods for executing and controlling microfluidic processes.

Within a living cell, there are several thousand substances required to assure a proper biological functionality. These substances include, for example, proteins, lipids, carbohydrates, nucleic acids, and small molecule metabolites. A number of techniques have been developed for analyzing these biological substance classes, such as two-dimensional gel electrophoresis or liquid chromatography followed by mass spectrometry. Besides this, science is still aiming for apparatuses and instruments helping to improve the performance of synthesis and analysis with respect to an efficient time/money to product ratio.

For this purpose, it is well known in the art to integrate microfluidic processes on chips. Such chips comprise commonly a sample inlet and a functional/detection area. Highly integrated processes can be executed, for example, with multilayer plastic chips comprising a structure, as disclosed for example in the U.S. Pat. No. 5,500,071 or U.S. Pat. No. 6,613,560.

Microfluidic devices can be used for example for the electrophoretic and analysis of DNA, RNA, and proteins or for executing a chromatographic process, for example a reversed phase column separation, followed by mass spectrometry. Another possibility to analyze samples known in the field is to provide microfluidic devices with an optical detection area. They normally comprise a microfluidic structure and can be adapted for executing an electrophoresis analysis process. Chips fitted out with an optical detection area commonly comprise transmissible material, in particular glass layers, with an inserted fluid conducting structure. Microfluidic chips comprising glass are disclosed for example in the U.S. Pat. No. 6,495,104 B1.

DISCLOSURE OF THE INVENTION

It is an object of the invention to provide an improved executing and/or controlling of microfluidic processes. The object is solved by the independent claims. Preferred embodiments are shown by the dependent claims.

According to the present invention, the objects indicated are achieved by a microfluidic assembly for executing and controlling microfluidic processes with at least one microfluidic flow path coupled to at least one inlet port. The assembly comprises two microfluidic devices, wherein at least one microfluidic device is adapted for executing a microfluidic process. Advantageously, the devices are coupled by an interface.

Embodiments may also include one or more of the following. The interface couples the two microfluidic devices fluidically. The interface can be realized by bonding, gluing, pressing against, or alike. The assembly or rather the devices of the assembly can be used for microfluidic laboratory technology for chemical, physical, and/or biological analysis, separation, reaction or synthesis of substances on a substrate with a microfluidic structure. The interface can be adapted for coupling at least one flow path of a first microfluidic device to at least one flow path of a second microfluidic device. Advantageously, this results in a highly integrated and miniaturized system, because two different microfluidic processes can be executed with the devices and coupled by the flow paths. Integration and miniaturization provides systems requiring just a small volume of reagents and samples, which is an important advantage when the required material is rare and/or expensive. Besides this, miniaturized systems generally provide improved performance characteristics.

The interface can be adapted for flow-controlling the flow within the first and the second flow path, in particular for connecting and disconnecting the first and the second flow path. This enables executing two separate processes. A first process can be for example a sample cleanup, PCR amplification, synthesis or hybridization process that needs to be physically separated from a second device in which a different second process is carried out. After finishing the initial first process, the flow paths can be coupled and the product of this initial process can be conducted to the subsequent second process, for example an analysis procedure or a further-processing step, via the coupled flow paths.

Advantageously, the interface comprises a valve, in particular a sliding valve with a slider, for flow-controlling the flow within the first and the second flow paths. The flow paths simply can be connected or rather disconnected by moving, in particular by sliding and/or rotating, the slider of the valve.

Additionally, the valve can be adapted for executing a microfluidic process, for example by a flow path comprising a substrate comprising a suitable material. The first microfluidic device can comprise plastic material or other suited materials, in particular flexible plastic material, preferably polyimide. Polyimide can be used for realizing microfluidic structures and reaction chambers for a plurality of microfluidic processes. The second microfluidic device can comprise a transmissible material, in particular glass, having a microfluidic structure comprising the flow path. Glass is well suited for analyses that require an optical detection, especially in combination with electrophoretic processes. This allows combining the advantages of both materials in one complete microfluidic process. In spite of the relatively high fluorescence of the suitable plastic material, for example polyimide, of the first microfluidic device, the microfluidic assembly or rather one of the devices of the assembly can comprise an optical detection area. Component processes, each executed with one microfluidic device, can be combined to a complete process. Handling of intermediate products is not necessary. Any soiling or contamination of the samples by manual handling is not possible.

The processes can be controlled by the interface or rather by the interconnected sliding valve. In other embodiments, the second microfluidic device can comprise a non-optical detection area, for example a conductivity sensor, and possibly a non-transmissible material. Advantageously, the first microfluidic device comprising the plastic material includes the valve. Plastic, for example polyimide is well suited for sealing purposes and can resist necessary sealing forces. Besides this, plastic can be coated with surface modifying material and/or material having a low friction coefficient, for example Teflon®.

The invention further relates to a method of preparing and analyzing a sample with a microfluidic assembly. In a first step, a sample is loaded to an inlet port of the assembly. Subsequently, at least one biochemical process is executed within the assembly. Finally, at least a part of the sample is transported from one microfluidic device to another microfluidic device via the interface.

Embodiments may include one or more of the following. Two microfluidic processes executed with the assembly can be combined by this method. The assembly comprises at least two microfluidic devices and an interface adapted for coupling the two microfluidic devices. The interface can realize at least two different settings, for example connecting the devices or disconnecting the devices.

Advantageously, the first biochemical process comprises a step of synthesizing and/or preparing or rather cleaning of a sample. The processed resulting sample of this step can be transported to an analytical area, in particular an electrophoresis separation channel with a detection area, of the assembly.

Especially advantageously, the process variables of the first biochemical process can be monitored. For this purpose, part of the sample can be transported to the analytical area in equal time-phases. The sample can be transported hydrodynamically and/or electrically. For controlling the flow of the sample, the setting of the interface can be changed.

Advantageously, the sample can be confined in a reaction chamber during processing the first biochemical process, for example by the interface or rather by a valve of the interface.

Embodiments may also include one or more of the following. The first biochemical process within the assembly can be executed while transporting at least part of the sample from one microfluidic device to another microfluidic device via the interface.

Advantageously, the interface can be adapted for executing the process. The interface can comprise a valve with a flow path comprising a substrate for executing a biochemical process. The sample can be transported through the flow path and processed, for example enriched or rather captured on the substrate and/or washed and/or eluted from the substrate, concurrently. For each of the steps of enriching or rather capturing, washing, and eluting the substrate, the setting of the valve can be changed. The valve can be realized by a slider.

Advantageously, the slider can realize a valve with more than two settings, for example an optional-route valve. Undesirable by-products, for example from the capturing and washing process can be directed to the waste. The eluted sample can be directed to an analytical (or further processing area, in particular an electrophoresis separation channel with a detection area, of the assembly.

Embodiments may also include one or more of the following. Advantageously, at least one PCR-cycle can be executed within the assembly, more precisely within a microfluidic device of the assembly. The assembly can comprise a reaction chamber adapted for executing the PCR-reaction. The interface can be closed for confining the sample in the reaction chamber, for example to avoid any evaporation of the sample. After executing the PCR-reaction, the chamber can be opened by the interface for transporting at least part of the sample to another microfluidic device of the assembly via the interface. The other microfluidic device of the assembly can comprise the electrophoresis column and a detection area.

Advantageously, the interface can be opened after each cycle of the PCR-reaction for transporting part of the sample to the electrophoresis column and the detection area for monitoring the complete PCR-process.

Especially advantageously, the sample loaded to the inlet port can comprise different molecules to be amplified. The molecules can be amplified and analyzed concurrently within the assembly. Costly separating and/or handling processes are not necessary.

Instead of the PCR-reaction, any other biochemical process, for example a hybridization or enzymatic reaction of the sample can be executed within the assembly or rather within the reaction chamber of one device of the assembly. Besides this, any other analysis procedure, for example the method of flow cytometry, can be executed within the assembly.

BRIEF DESCRIPTION OF DRAWINGS

Other objects and many of the attendant advantages of embodiments of the present Invention will be readily appreciated and become better understood by reference to the following more detailed description of preferred embodiments in connection with the accompanied drawings. Features that are substantially or functionally equal or similar will be referred to with the same reference signs.

FIG. 3 shows a three dimensional top plan view of another microfluidic assembly with a sliding valve;

FIGS. 4 and 5 show a cross sectional view of the assembly of FIG. 3 in two different settings, taken along the lines IV-IV of FIG. 3.

FIG. 1 shows a top plan view of a microfluidic assembly 1 with an optional-route sliding valve 3 realizing an interface 5. The interface 5 is adapted for coupling a first microfluidic device 9 and a second microfluidic device 7 of the microfluidic assembly 1. FIG. 2 shows a longitudinal view of the assembly 1 of FIG. 1, taken along the lines II-II of FIG. 1. Not visible parts within the microfluidic assembly 1 are illustrated dotted.

Figure 1:
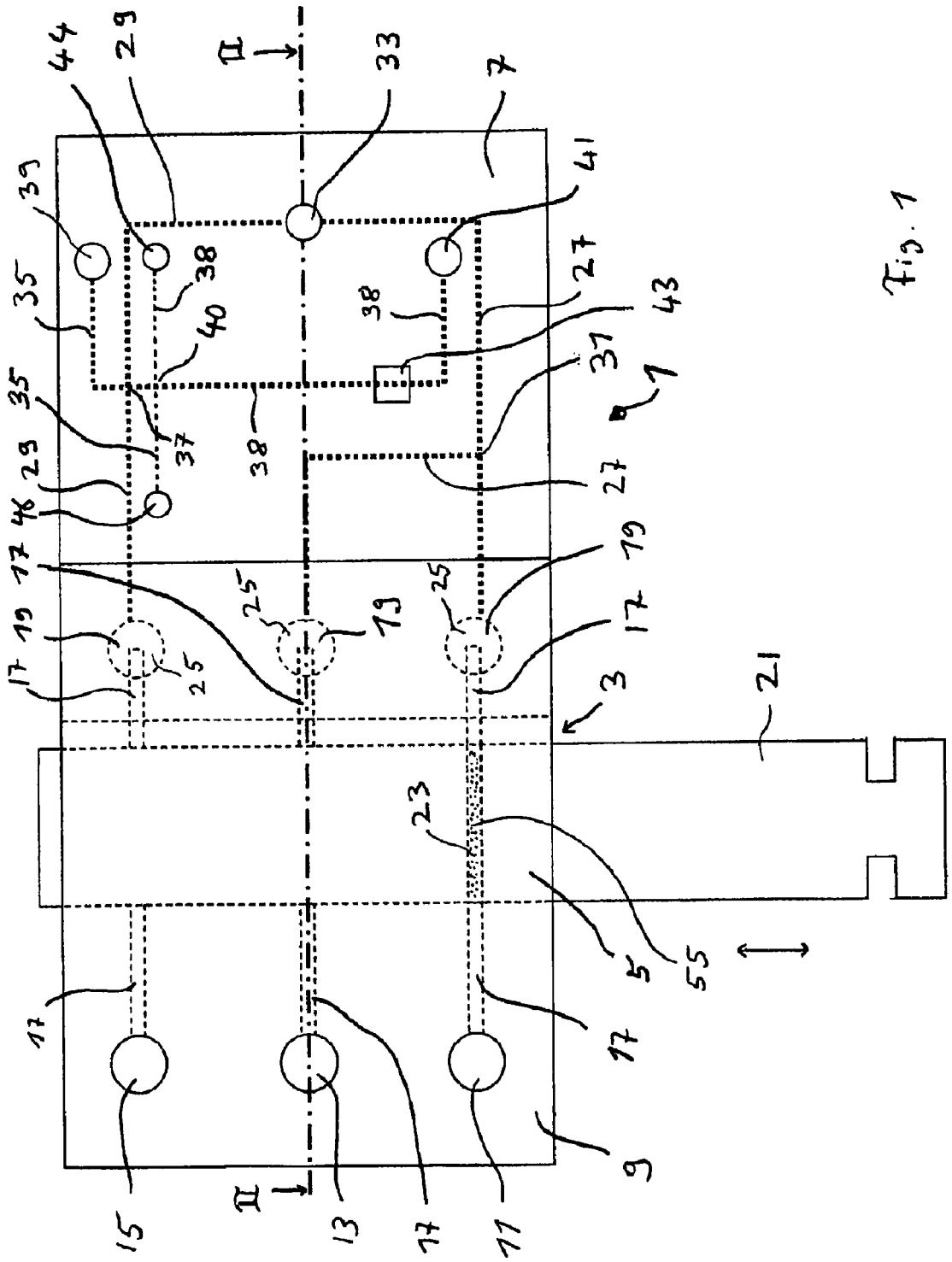
FIG. 1 shows a top plan view of a microfluidic assembly with an optional-route sliding valve.

The first microfluidic device 9 comprises three ports, a sample inlet port 11, a processing reagent (for example wash solution) port 13, and an sample elution port 15. The ports 11, 13, and 15 each can be coupled to a corresponding interface port 19 via flow paths 17 and via the interface 5. The first microfluidic device 9 comprises three interface ports 19 each coupled to one of the three flow paths 17.

Figure 2:
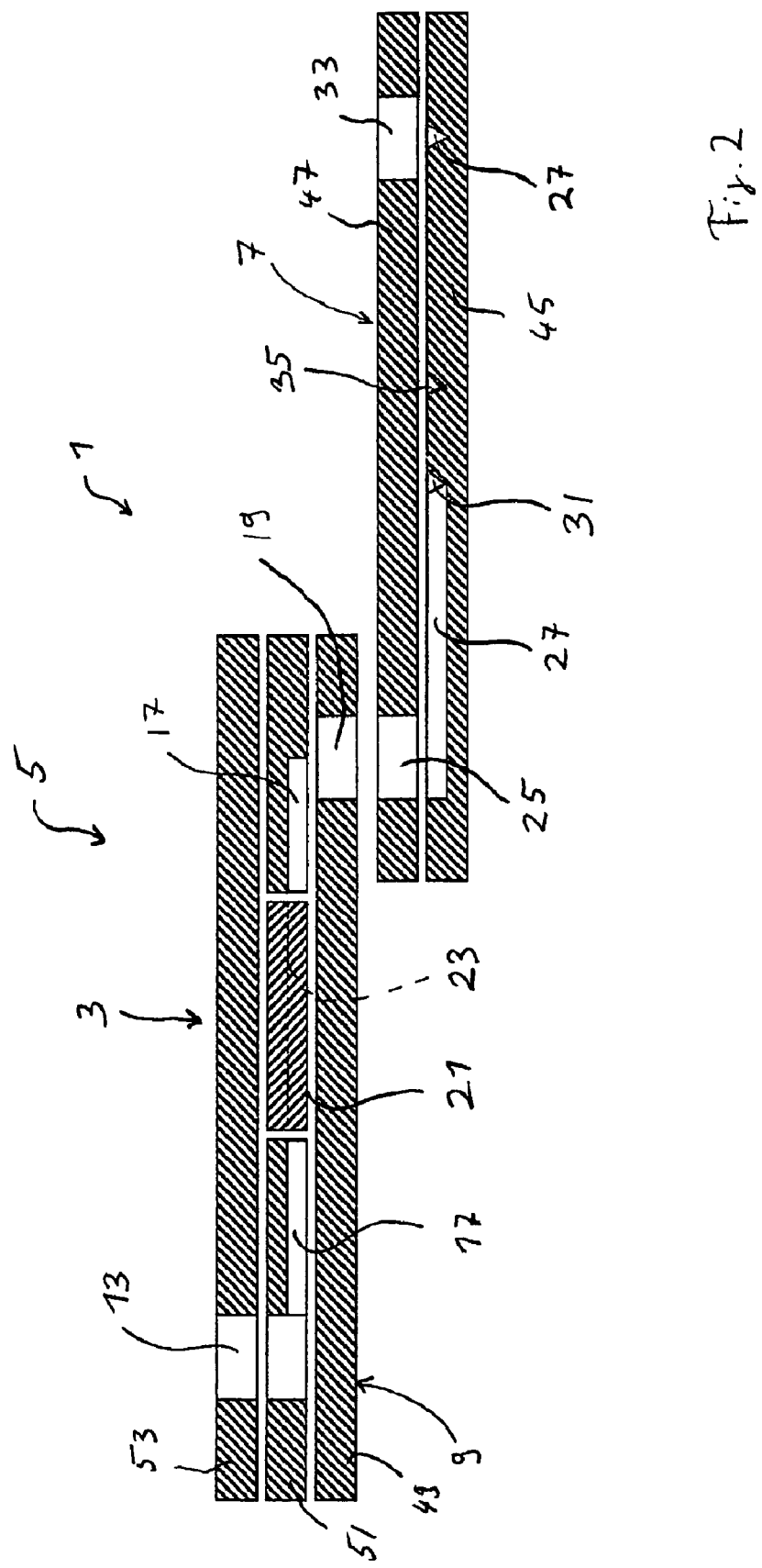
FIG. 2 shows a longitudinal view of the assembly of FIG. 1, taken along the lines II-II of FIG. 1.

The optional-route sliding valve 3 of the interface 5 of the first microfluidic device 9 comprises a slider 21 with a linking flow path 23. The slider 21 can be slit perpendicularly to the picture plane of FIG. 2 for changing the setting of the optional-route sliding valve 3. The optional-route sliding valve 3 can connect the ports 11, 13, and 15 optionally to one of the corresponding interface ports 19.

The second microfluidic device 7 is coupled to the first microfluidic device 9 at the interface region 5, for example by bonding, gluing, pressing against, or alike. The second microfluidic device 7 comprises also three interface ports 25 coupled to the interface ports 19 of the first microfluidic device 9. Two of the three interface ports 25 are coupled to a waste flow path 27 of the second microfluidic device 7 and one of the three interface ports 25 is coupled to an elution flow path 29. The waste flow path 27 comprises a forking 31, wherein two branches of the waste flow path 27 are coupled to the interface ports 19 and one branch is coupled to a vacuum port 33 of the second microfluidic device 7. The elution flow path 29 of the second microfluidic device 7 crosses a sample pre-draw electrophoresis path 35 of the second microfluidic device 7 at a crossing point 37. Besides this, the second microfluidic device 7 comprises a sample separation electrophoresis path 38 adapted for separating the components of the sample.

The electrophoretic sample pre-draw path 35 and the electrophoretic sample separation path 38 each are coupled to a pair of electrode ports 39, 46 and 41, 44. The ports 39, 46 and 41, 44 each can be coupled to a not shown voltage source for transporting or rather separating the components of the sample within the electrophoretic sample pre-draw path 35 and the electrophoretic sample separation path 38. The sample pre-draw path 35 and the sample separation path 38 each comprise an angular layout and intersect at an injection cross 40. The sample pre-draw path 35 and the sample separation path 38 each are angled at the injection cross 40.

The second device 7 comprises nearby and/or within the sample separation electrophoresis path 38 a detection area 43. The detection area 43 is adapted for analyzing the sample, in particular for detecting peaks, within the sample separation electrophoresis flow path 38, for example electrically and/or optically with according sensors.

The second microfluidic device 7 comprises a bottom glass layer 45 and a top glass layer 47. The bottom glass layer 45 comprises a microfluidic structure with the waste flow path 27, the elution flow path 29, the sample pre-draw electrophoresis flow path 35, and the sample separation electrophoresis flow path 38. The second microfluidic device 7 is adapted for executing an analytical process, in this case an electrophoresis separation.

The first microfluidic device 9 comprises three layers, a bottom layer 49, a structure layer 51, and a top layer 53. The structure layer 51 of the first microfluidic device 9 comprises a microfluidic structure—realized by fluid conducting grooves, slits, or alike—with the flow paths 17. The layers 49, 51, and 53 of the first microfluidic device 9 comprise a plastic, for example a flexible plastic as polyimide. The first microfluidic device 9 is adapted for executing a biochemical sample preparation or modifying process. Therefore, the linking flow path 23 comprises a substrate 55 adapted for binding or modifying components of a sample, for example binding DNA or proteins. Therefore, the substrate can comprise or consist of silica particles, immobilized antibodies, Ni-EDTA-beads for capturing His-tagged proteins, beads coupled with specific oligonucleotides for capturing of DNA-binding proteins, or alike.

Analytical electrophoresis separation processes executable with chips comprising transmissible layers and a microfluidic structure, chips comprising glass layers, biochemical sample preparation processes, and microfluidic chips comprising plastic layers are known in the art. Therefore, in the following only the specific functional details of the microfluidic assembly 1 are described in detail:

The microfluidic assembly 1 is adapted for executing a complete biochemical sample preparation or modifying and a subsequent analysis process. Consequently, this complete process can be executed in just one device.

The process can be controlled by the optional-route sliding valve 3 of the interface 5 realizing three relevant settings:

In a first setting of the optional-route sliding valve 3 of the interface 5, the sample inlet port 11 of the first microfluidic device 9 is coupled to the vacuum port 33 of the second microfluidic device 7 of the microfluidic assembly 1 via one of the flow paths 17, via the linking flow path 23 of the slider 21 comprising the substrate 55, via one of the interface ports 19 of the first microfluidic device 9, via one of the three interface ports 25 of the second microfluidic device 7, and via one branch and the forking 31 of the waste flow path 27 of the second microfluidic device 7.

In the first setting, a sample, for example a cell lysate, can be transported through the substrate 55 for binding relevant components of the sample.

In a second setting, the processing reagent port (for example containing a wash solution) 13 of the first microfluidic device 9 is coupled to the vacuum port 33 of the second microfluidic device 7 of the microfluidic assembly 1 via the flow paths 17, via the linking flow path 23 comprising the substrate 55 of the slider 21, via one of the interface ports 19 of the first microfluidic device 9, via one of the three interface ports 25 of the second microfluidic device 7, and via the other branch and the forking 31 of the waste flow path 27 of the second microfluidic device 7.

In the second setting, the substrate 55 with the adsorbed components of the sample can be flushed with a reagent or a buffer, for example a wash solution.

In a third setting, the sample elution port 15 of the first microfluidic device 9 is coupled to the vacuum port 33 of the second microfluidic device 7 of the microfluidic assembly 1 via one of the flow paths 17, via the linking flow path 23 comprising the substrate 55 of the slider 21, via one of the interface ports 19 of the first microfluidic device 9, via one of the three interface ports 25 of the second microfluidic device 7, and via the elution flow path 29 crossing the sample pre-draw electrophoresis flow path 35 at the crossing point 37.

In the third setting, the processed sample or rather the washed relevant components of the sample being bound to the substrate 55 can be eluted and transported to the crossing point 37 of the second microfluidic device 7. The paths 35 and 38 can comprise a gel, for example polyacrylamide. For executing an analysis process with the second microfluidic device 7, a voltage can be applied to the gel via the ports 39, 46 and 41, 44. The sample can be analyzed directly by the detection area 43.

The sample processing or preparation process and the analysis process both can be executed with the microfluidic assembly 1. The complete process can be controlled just by setting the optional-route sliding valve 3. For preparing the microfluidic assembly 1, the ports 11, 13, and 15 of the first microfluidic device 9 have to be supplied with the according liquids, a vacuum has to be applied to the vacuum port 33, and a voltage has to be applied to the gel within the sample pre-draw electrophoresis path 35 and the sample separation path 38 of the second microfluidic device 7. Additional steps, for example feeding the prepared sample to a single electrophoresis device, are not necessary.

Alternatively, the ports 11, 13, and 15 can be supplied with the according liquids under pressure for transporting them through the devices 7 and 9. Additionally, the vacuum can be applied to the vacuum port 33.

In embodiments, a layer or rather a flow path of the first microfluidic device 9 can comprise the substrate 55. The slider 21 can realize a multi-route switching valve adapted for coupling the ports 11, 13, and 15 optionally to the flow path containing the substrate 55. In further embodiments, the slider 21 can be substituted by an external rotating multi-route switching valve. In other embodiments, the ports 11, 13, and 15 are substituted by one single port fed with the different liquids.

In further embodiments, the slider 21 of the first microfluidic device 9 is changeable and/or disposable. Consequently, the microfluidic assembly 1 can be adapted for preparing different samples, for example containing DNA or proteins to be analyzed. For this purpose, different sliders 21 can comprise different substrates 55 with different specifications. For the same advantages, in other embodiments, the first microfluidic device 9 is separatable from the second microfluidic device 7 and/or disposable.

The different liquids can be transported by applying a vacuum to the vacuum port 33. In embodiments, the transportation can be induced by any hydrodynamic transportation device, for example by a nano pump, or by a voltage source.

FIG. 3 shows a three dimensional top plan view of a microfluidic assembly 57 with a sliding valve 59. FIGS. 4 and 5 show a cross sectional view of the assembly 57 of FIG. 3 in two different settings, taken along the lines IV-IV of FIG. 3. The principal setup of the microfluidic assembly 57 is similar to the setup of the microfluidic assembly 1 as shown above. Therefore, in the following briefly the differences are described. Not visible parts within the microfluidic assembly 57 are illustrated dotted.

The microfluidic assembly 57 comprises a second microfluidic device 61 and a first microfluidic device 63 coupled by an interface 65. The interface 65 of the microfluidic assembly 57 comprises the sliding valve 59 and two contact planes, a first contact plane 67 of the top glass layer 47 of the second microfluidic device 61 and a second contact plane 69 of the bottom layer 49 of the first microfluidic device 63. The contact planes 67 and 69 of the microfluidic assembly 57 are glued, bonded, pressed together, or alike.

The layers 47 and 49 of the microfluidic assembly 57 each comprise congruent 4×4 patterns 71 of sixteen through holes 73, for example through bores. The structure layer 51, the top layer 53, and an additional separating layer 75 each comprise congruent 3×4 patterns 77, also with through holes 73. Compared to the congruent 4×4 patterns 71, the congruent 3×4 patterns 77 comprise only twelve through holes 73, more precisely one row of four through holes 73 less. The through holes 73 of the patterns 71 and 77 of the layers 47, 49, 75, 51, and 53 of the microfluidic assembly 57 are matched together for realizing twelve ports 79 for the second microfluidic device 61. The ports can be adapted as wells for feeding microfluidic flow paths, for example inserted in the bottom glass layer 45 or in the top glass layer 47 of the second microfluidic device 61, or as fluid transporting ports for example for applying pressure, vacuum, or for applying a voltage. The microfluidic structure and the ports 79 of the second microfluidic device 61 can be adapted for executing an analytical process, for example, an electrophoresis separation process with an optical detection area as described above.

The first microfluidic device 63 comprises an inlet port 81 coupled to an inlet flow path 82, a reaction chamber 83 comprising a loop flow path 85. The bottom layer 49 and the top glass layer 47 of the microfluidic assembly 57 comprise each four interface ports 87 realized by one row of four through holes 73 of the congruent 4×4 patterns 71. The slider 21 of the sliding valve 59 comprises a row of four corresponding through bores 89. In embodiments, the through bores 89 can be substituted by any through hole having any shape. For opening and closing the four interface ports 87 of the interface 65 or rather the sliding valve 59 of the microfluidic assembly 57, the slider 21 can be slit rectilinearly as illustrated with an arrow 90, for example in a first setting and in a second setting. In embodiments, the slider 21 can be realized as a rotor comprising the according through bores.

In the first setting, as illustrated in FIG. 4, all interface ports 87 are opened and coupled to the flow paths 82 and 85. In this setting, the first microfluidic device 63 is coupled fluidically to the second microfluidic device 61. A sample can be loaded to the reaction chamber 83 via the inlet port 81, via one of the through bores 89 of the slider 21, via one of the four interface ports 87 of the bottom layer 49 of the first microfluidic device 63 and of the top glass layer 47 of the second microfluidic device 61, via a not shown flow path of the second microfluidic device 61, via another one of the four interface ports 87 of the bottom layer 49 of the first microfluidic device 63 and of the top glass layer 47 of the second microfluidic device 61, via another one of the through bores 89 of the slider 21, and via the loop flow path 85. For transporting the liquid sample, one end of the loop flow path 85 of the reaction chamber 83 can be coupled to a vacuum port of the second microfluidic device 61 via the interface 65 of the microfluidic assembly 57.

In the second setting, the four interface ports 87 are closed. Consequently, a reaction agent can be confined within the reaction chamber 83 for executing a biochemical process, for example, a PCR or a hybridization process as known in the art being therefore described just schematically in this application. For executing a PCR-process, the first microfluidic device 63 can be brought in contact with a peltier-element 91 for controlling the necessary temperature cycles within the reaction chamber 83. Advantageously, the plastic layers 49, 75, 51, and 53 of the first microfluidic device 63 have a favorable temperature coefficient compared to the glass layers 45 and 47 of the second microfluidic device 61. The second microfluidic device 61 comprises a transmissible material, well suited for an optical detection combined with an electrophoresis analysis process. Consequently, the microfluidic devices 61 and 63 can be combined to an advantageous assembly adapted for processing a complete microfluidic biochemical analysis process.

In embodiments, the temperature cycles of the PCR-process are controlled by any other heating and/or cooling device, for example by an infrared device, a liquid cooling/heating circuit, a ventilating fan, heated air ventilator, conventional electrical heating wires, or alike.

In embodiments, part of the prepared sample can be transported from the reaction chamber 83 of the first microfluidic device 63 to the second microfluidic device 61 after each cycle or after an arbitrary amount of cycles of the PCR-process thus enabling monitoring the progress of the PCR reaction. The amount of the drawn sample can be controlled by opening and closing the sliding valve 59 of the microfluidic assembly 57.

In embodiments, the sliding valve 59 of the microfluidic assembly 57 interacts with actuators 93. The actuators 93 can apply sealing forces to the sliding valve 59, for example by piezo-elements, springs, magnets, or alike. For sliding the slider 21 of the sliding valve 59, the actuators 93 can be released for reducing the friction between the slider 21 and the layers 49 and 51.

In further embodiments, the first microfluidic device 63 comprises instead of the reaction chamber 83 just a reaction flow path 95. The reaction flow path 95 is coupled to an inlet port 97, to one of the four interface ports 87 and to one of the through holes 73 of the congruent 4×4 patterns 71 for controlling the biochemical processes executable with the microfluidic assembly 57. The two through holes 73 nearby the reaction flow path 95 of the congruent 3×4 patterns 77 of the top layer 53 and of the structure layer 51 of the first microfluidic device 63 are closed for coupling the reaction flow path 95 to one of the ports 79 of the second microfluidic device 61. More precisely, the reaction flow path 95 is coupled directly—without any flow-controlling by the slider 21—to this port 79.

In other embodiments, the reaction flow path 95 comprises additionally a forking 99 coupled to the inlet port 97 of the first microfluidic device 63 and to a second port 101—illustrated dotted—of the first microfluidic device 63. For soaking a liquid sample into the reaction flow path $95_i$ a vacuum can be applied to one of the ports 97 or 101. The other one of the ports can be fed with the sample.

In embodiments, the microfluidic structure of the microfluidic assembly is realized by laser, by scribing, by etching, or alike.

In other embodiments, the first microfluidic device 9 is adapted just for flow-controlling the flow within at least one interface port of the second microfluidic device 7.

In further embodiments, the microfluidic assembly can be covered with a caddy for convenient handling and for protecting the microfluidic assembly. The caddy comprises connectors and guides for a laboratory apparatus.

In the following, single steps of methods of preparing and analyzing a sample—in embodiments executable with the microfluidic assembly as shown above—are described schematically and exemplarily:

Before analyzing a biological sample (For example animal tissue or cultured cells) using a microfluidic (or other) device usually a sample cleanup has to be done. In this procedure the molecules of interest (for example DNA, RNA, or proteins) are separated from the other substances included in the crude sample prior to the subsequent analysis. Many methods for isolating different biomolecule classes have been developed. For example, DNA or RNA can be isolated from biological samples using adsorption matrices (for example silica) that bind nucleic acids. Therefore, the crude sample is applied to the binding material, typically included in a spin column, followed by one or more wash steps. After that, the adsorbed DNA or RNA can be removed from the adsorption matrix using an elution solvent. Typical downstream applications of isolated nucleic acids are for example sequencing, cloning, or hybridization reactions. One of the most important techniques for analyzing or amplifying DNA samples is the polymerase chain reaction (PCR). Using this method, undetectable amounts of DNA can be amplified exponentially, resulting in sufficient amounts for a subsequent analysis or preparation. (The technique is described in the U.S. Pat. No. 4,683,195 to Mullis et al. and in related publications, for example in the U.S. Pat. No. 4,683,202, U.S. Pat. No. 4,800, 159, and U.S. Pat. No. 4,965,188 to Mullis et al.).

The PCR-process is executed in a device called thermo cycler, (see US 2003/0169799 A1), in which multiple temperature cycles are applied to the reaction mix usually a typical PCR cycle consists of 3 different temperature steps. In the first step, the DNA sample is denatured at about 94° C. The second step "primer annealing", is performed at a temperature in the range of 40-65° C. and in the third step the DNA synthesis is carried out at approximately 72° C. Due to the nucleotide sequence of the primers that are used for the PCR reaction only a specific DNA templates of the sample are amplified, thus leading to the enrichment of one (or more) distinct DNA fragments. Theoretically, the amount of the amplified DNA fragments is doubled in each cycle.

On the other hand, an often-discussed problem in the field is the effect that the amplification efficiency is not constant for all conducted PCR cycles, therefore leading to a non-linearity of the reaction and the inability to quantitate the original DNA template. To address this problem, methods measuring derived physical quantities for monitoring the PCR-process such as sample fluorescence have been developed, known as quantitative Real-Time PCR [see also: Bustin S A; J Mol Endocrinol. 2002 August; 29(1):23-39; Quantification of mRNA using real-time reverse transcription PCR (RT-PCR): trends and problems.]. PCR is used for a variety of biological, medical, and pharmaceutical applications including pathogen detection, forensics, genotyping, and clinical diagnostics.

Other methods, for example methods known as "southern blot" or "northern blot", use a hybridization step to analyze and quantitate a special DNA or RNA specimen within a nucleic acid sample. Hybridization is the specific complementary association due to hydrogen bonding of single-stranded nucleic acids under experimental conditions. It can be also referred to as "annealing", as this is the physical process responsible for the association. Two complementary sequences will form hydrogen bonds between their complementary bases (G to C, and A to T or U). This results in a stable double-stranded, anti-parallel "hybrid" molecule. The hybridization can be used for marking specific single-stranded DNA sequences of interest for an analysis.

The prepared and/or amplified sample can be analyzed, for example be fed to a microfluidic device as described above directly or via an automatic sampler.

For carrying out a complete analysis of a sample, many single processes, for example processes for preparing and/or analyzing as described above, have to be executed. Such samples are very susceptible to any soiling and contamination or user mishandling.

In the following, a method enabling preparing and analyzing a susceptible sample with just one microfluidic assembly is described by referring to the single steps of methods of preparing and analyzing a sample as described above and to the Figures:

Any soiling and contamination or user mishandling of the sample can be avoided with this method. In a first step, referring to the FIGS. 3 to 4, a sample is loaded to an inlet port 81 of the microfluidic assembly 57. Subsequently, a first biochemical process is executed within the microfluidic assembly 57. Finally, at least part of the sample is transported from the first microfluidic device 63 to the second microfluidic device 61 via the interface 65 of the microfluidic assembly 57.

In other embodiments, the sample can be transported before the first biochemical process is executed or while the first biochemical process is executed.

In other embodiments, the sample can be transported before the first biochemical process is executed or while the first biochemical process is executed. This method can also be executed with the microfluidic assembly 1 as shown in the FIGS. 1 and 2.

In embodiments, the method has to be executed at least three times for executing the complete process executable with the microfluidic assembly 1. The sample is loaded for each repetition to one of the ports 11, 13, and 15 of the first microfluidic device 9. The first biochemical processes of the three repetitions correspond to the steps of binding a sample to the substrate 55 contained in the slider 21 of the first microfluidic device 9, washing the substrate 55 and the sample, and eluting the sample from the substrate 55 and is executed concurrently to the step of transporting the sample.

In further embodiments, the first biochemical process is executed within the microfluidic assembly 1 or more precisely within the linking flow path 23 of the slider 21 while at least part of the sample is transported from the first microfluidic device 9 to the second microfluidic device 7 via the interface 5.

In embodiments, the prepared sample is transported to an analytical area—or more precisely to the crossing point 37 of the sample pre-draw electrophoresis path 35 and within the paths 35 and 38 to the detection area 43 of the second microfluidic device 7.

In further embodiments, the setting of the interface of the microfluidic assembly is changed after executing the first biochemical process. For executing this step with the microfluidic assembly 57, the slider 21 of the sliding valve 59 can be moved and/or rotated in two relevant settings. The sliding valve 59 of the microfluidic assembly 57 can be opened or closed by moving the slider 21. The biochemical process can be for example one or more cycles of the PCR process executed within the reaction chamber 83 of the first microfluidic device 63 of the microfluidic assembly 57.

In embodiments, the sliding valve 59 of the interface 65 can be closed before and opened after executing at least one PCR-cycle. Advantageously, the PCR-process can be monitored by the downstream analysis process executable with the second microfluidic device 61.

In embodiments, a sample with different molecules can be loaded to the inlet port 81 of the first microfluidic device 63 for amplifying the molecules concurrently with just one PCR-process.

In embodiments, the method is executed with the microfluidic assembly 1 with the additional subsequent steps as follows: The interface 5 of the microfluidic assembly 1 is brought in the first setting; the sample is loaded to the sample inlet port 11; and transported to the substrate 55. Subsequently, the interface 5 is brought to a second setting. After that, a wash solution is loaded to the processing reagent port 13 of the first microfluidic device 9. Subsequently, the interface 5 is brought in the third setting. Finally, an elution solvent is loaded to the sample elution port 15 of the first microfluidic device 9 for eluting the sample from the substrate 55.

In embodiments, at least a part of the sample is transported from the first microfluidic device to the second microfluidic device via the interface before or while executing the first biochemical process within the assembly. The first microfluidic device can be adapted just for flow-controlling. Consequently, just one biochemical process can be executed with the microfluidic assembly and controlled by the first microfluidic device of the microfluidic assembly.

In embodiments, the microfluidic assembly can comprise more than two microfluidic devices. The microfluidic devices can be coupled by one or more interfaces adapted for coupling the microfluidic devices. Consequently, the microfluidic assembly can be adapted for executing an arbitrary amount of biochemical and/or analytical processes. The processes can be series-connected and/or parallel-connected via the interfaces and the microfluidic devices of the microfluidic assembly.

It is to be understood that this invention is not limited to the particular component parts of the devices described or to process steps of the methods described as such devices and methods may vary. It is also to be understood, that the terminology used herein is for purposes describing particular embodiments only and it is not intended to be limiting. It must be noted that, as used in the specification and the appended claims, the singular forms of "a", "an", and "the" include plural referents until the context clearly dictates otherwise. Thus, for example, the reference to "a microfluidic device" or "a slider" includes two or more such functional elements.

The invention claimed is:

1. A microfluidic assembly comprising:
    two microfluidic devices, wherein at least one of the microfluidic devices is configured for executing a microfluidic process,
    wherein one of the two microfluidic devices comprises a valve, coupled to the other microfluidic device, the valve comprising a structure layer interposed between a bottom layer and a top layer, wherein the structure layer comprises a planar substrate having a first flow path that selectively connects a plurality of second flow path formed therein that selectively connects a plurality of second flow paths between the two microfluidic devices.

2. The assembly of claim 1, wherein the valve is configured to control a flow within the at least flow path by selectively connecting and/or disconnecting the at least one flow path.

3. The assembly of claim 1, wherein the structure layer comprises an optional-route slider.

4. The assembly of claim 1, wherein the structure layer comprises a slider configured for at least one of sliding relative to, sliding rectilinearly to, or rotating relatively to, at least one of the microfluidic devices.

5. The assembly of claim 1, wherein the valve comprises at least one microfluidic control element for controlling a flow within the at least one flow path.

6. The assembly of claim 1, wherein at least one of the microfluidic devices comprises an optically transmissible material.

7. The assembly of claim 1, wherein the valve is an integrated part of one of the microfluidic devices.

8. The assembly of claim 1, wherein a first one of the microfluidic devices is adapted for executing a first microfluidic process, and wherein a second one of the microfluidic devices is adapted for executing a second microfluidic process.

9. A microfluidic assembly comprising:
    two microfiuidic devices, wherein at least one of the microfluidic devices is configured for executing a microfluidic process,
    wherein one of the two microfluidic devices comprises a valve, coupled to the other microfluidic device, the valve comprising a structure layer interposed between a bottom layer and a top layer, wherein the structure layer is configured to provide at least one selectively connectable flow path between the two microfluidic devices,
    wherein the structure layer comprises a slider configured for at least one of sliding relative to, sliding rectilincarly to, or rotating relatively to, at least one of the microfluidic devices.

10. Method of preparing and analyzing a sample with a microfluidic assembly, comprising:
    loading a sample to an inlet port of the microfluidic assembly,
    executing a first biochemical process within a first microfluidic device of the microfluidic assembly, and
    transporting at least part of the sample from the first to a second microfluidic device of the microfluidic assembly via a structure layer interposed between a bottom layer and a top layer of a valve incorporated in one of the first and second microfluidic devices, before, while, or after executing the first biochemical process.

11. Method of claim 10, further comprising: transporting at least part of the sample to at least one of an analytical area, an electrophoresis channel and a detection area, of the microfluidic assembly.

12. Method of claim 10, further comprising: changing a setting of the valve after executing the first biochemical process.

13. Method of claim 10, further comprising:
    bringing the valve of the microfluidic assembly to a first setting,
    loading a sample in a sample inlet port of the microfluidic assembly,
    bringing the sample in contact with a binding and/or adsorbing material,
    bringing the valve to a second setting,
    loading a processing or washing reagent to a processing reagent port of the microfluidic assembly,
    bringing the valve to a third position,
    loading an elution solvent to a sample elution port of the microfluidic assembly, and
    eluting the sample.

14. Method of claim 13, further comprising: loading the ports by applying a vacuum to a vacuum port of the microfluidic assembly, by applying the according liquid under pressure to the ports, or by applying a voltage.

15. Method of claim 10, further comprising:
    closing the valve of the microfluidic assembly after loading the sample to the inlet port of the microfluidic assembly,
    executing at least one PCR-cycle within the microfluidic assembly,
    opening the valve of the microfluidic assembly before transporting at least part of the sample from the first microfluidic device to the second microfluidic device via the structure layer.

16. Method of claim 15, further comprising: loading a sample with different sample contents to be processed to the inlet port.

17. Method of claim 10, further comprising:
    opening the valve after each cycle of the PCR-reaction for transporting part of the sample and for monitoring the complete PCR-process.

18. Method of claim 10, further comprising:
    executing a hybridization process of the sample within the microfluidic assembly after loading the sample to the inlet port of the microfluidic assembly.

19. Method of claim 10, further comprising:
    executing a first microfluidic process within the structure layer,
    executing a second microfluidic process within the second microfluidic device.

* * * * *

UNITED STATES PATENT AND TRADEMARK OFFICE
CERTIFICATE OF CORRECTION

| | | |
|---|---|---|
| PATENT NO. | : 7,998,437 B2 | Page 1 of 2 |
| APPLICATION NO. | : 11/707429 | |
| DATED | : August 16, 2011 | |
| INVENTOR(S) | : Manfred Berndt et al. | |

It is certified that error appears in the above-identified patent and that said Letters Patent is hereby corrected as shown below:

In column 11, line 32, in Claim 2, after "within" delete "the".

In column 11, line 32, in Claim 2, delete "least" and insert -- least one of the plurality of second --, therefor.

In column 11, line 32, in Claim 2, delete "path" and insert -- paths --, therefor.

In column 11, line 33, in Claim 2, delete "at least one" and insert -- first --, therefor.

In column 11, line 41, in Claim 5, delete "at least one" and insert -- first --, therefor.

In column 11, line 48, in Claim 8, delete "adapted" and insert -- configured --, therefor.

In column 11, line 50, in Claim 8, delete "adapted" and insert -- configured --, therefor.

In column 11, line 52, in Claim 9, delete "microfiuidic" and insert -- microfluidic --, therefor.

In column 11, line 62, in Claim 9, delete "rectilincarly" and insert -- rectilinearly --, therefor.

In column 12, line 1, in Claim 10, delete "a" and insert -- the --, therefor.

In column 12, line 2, in Claim 10, delete "assembly," and insert -- assembly of claim 1, --, therefor.

In column 12, line 5, in Claim 10, delete "first" and insert -- first one of the two --, therefor.

In column 12, line 6, in Claim 10, delete "device of the microfluidic assembly," and insert -- devices, --, therefor.

In column 12, line 7, in Claim 10, delete "first" and insert -- first one --, therefor.

Signed and Sealed this
Third Day of January, 2012

David J. Kappos
*Director of the United States Patent and Trademark Office*

CERTIFICATE OF CORRECTION (continued)
U.S. Pat. No. 7,998,437 B2

In column 12, line 8, in Claim 10, delete "second" and insert -- second one of the two --, therefor.

In column 12, line 8, in Claim 10, delete "device of the microfluidic assembly" and insert -- devices --, therefor.

In column 12, line 9, in Claim 10, delete "a" and insert -- the --, therefor.

In column 12, lines 9-11, in Claim 10, after "layer" delete "interposed between a bottom layer and a top layer of a valve incorporated in one of the first and second microfluidic devices".